United States Patent [19]

Mimura et al.

[11] Patent Number: 5,132,294
[45] Date of Patent: Jul. 21, 1992

[54] ANTIOXIDATIVE GLYCOSIDE AND ANTIOXIDATIVE COMPOSITION CONTAINING THE SAME

[75] Inventors: Akio Mimura, Fuji; Keiichi Takebayashi, Tsukuba; Yoshimasa Takahara, Narashino; Toshihiko Osawa, Kasugai, all of Japan

[73] Assignee: Kabushiki Kaisha Kobe Seiko Sho, Kobe, Japan

[21] Appl. No.: 724,929

[22] Filed: Jul. 2, 1991

[30] Foreign Application Priority Data

Jul. 5, 1990 [JP] Japan .................................. 2-176436
Feb. 27, 1991 [JP] Japan .................................. 3-115714

[51] Int. Cl.$^5$ ...................... C09K 15/00; C07H 15/00; C07H 17/00
[52] U.S. Cl. ........................................ 514/53; 514/25; 536/4.1; 536/18.1; 252/397; 426/541
[58] Field of Search ....................... 536/4.1; 514/25, 53; 252/397; 426/541

[56] References Cited

PUBLICATIONS

Fukuda et al., *Agric. Biol. Chem.*, vol. 49(2), 1985, pp. 301–306.
Phytochemistry, vol. 25, No. 7, (1986), Yukihiro Shoyama et al, pp. 1633–1636 "Four caffeoyl glycosides from callus tissue of Rehmannia glutinosa".
Agricultural and Biological Chemistry, vol. 49, No. 2, 1985, Agricultural Chemical Society of Japan, Tokyo Y. Fukuda et al. "Studies on Antioxidative Substances in Sesam Seed" pp. 301–306.
Chemical Abstracts, vol. 115, Aug. 5, 1991, Columbus, Ohio, USA A. Mimura "Production of glycoside antioxidants by suspension cell culture of *Sesamum indicum* L." p. 668, abstract-No. 47 674 f & Fragrance J. 1991, 19(4), 96–101 (Japan).

*Primary Examiner*—Johnnie R. Brown
*Assistant Examiner*—Pamela S. Webber
*Attorney, Agent, or Firm*—Oblon, Spivak, McClelland, Maier & Neustadt

[57] ABSTRACT

The present invention relates to the antioxidative glycoside of structural formula (A) above-shown, obtained from the culture of growing cells derived from the plant body of sesame (*Sesamun indicum* L.), can provide the glycoside in large quantities by utilizing sesame, and also relates to an antioxidant comprising at least one substance of the glycoside of structural formula (A) above-shown as effective ingredient, the antioxidant being harmless and effective particularly for prevention of oxidation of foods, drugs, cosmetics, etc.

2 Claims, 19 Drawing Sheets

SUBSTANCE 1

SUBSTANCE 2

SUBSTANCE 3

SUBSTANCE 1

SUBSTANCE 2

SUBSTANCE 3

SUBSTANCE 3

SUBSTANCE 2

SUBSTANCE 3

SUBSTANCE 1

SUBSTANCE 2

SUBSTANCE 3

SUBSTANCE 1

SUBSTANCE 2

SUBSTANCE 3

ANTIOXIDATIVE GLYCOSIDE AND ANTIOXIDATIVE COMPOSITION CONTAINING THE SAME

FIELD OF THE INVENTION

The present invention relates to glycosides extracted from callus artificially derived from the plant body of sesame (Sesamum indicum L.) which has an anti-oxidative activity, relates to the process for preparing the same and also relates to the use thereof.

BACKGROUND OF THE INVENTION

In general, foodstuffs are prepared from agricultural products, marine products, livestock products, etc. However, during the course of storage or preservation processing of raw food materials or products, raw food materials or products are deteriorated by contamination and putrefaction with microorganisms or by chemical or physical action to reduce their commercial value. Therefore, a variety of food additives have been developed and at the same time, methods for a temperature treatment, an oxygen absorption treatment, vacuum packaging, low temperature storage, a radiation treatment, etc. have been developed and practically used.

The most serious problem in such deterioration of food materials or products is oxidation or peroxidation of food ingredients with oxygen in the air. Oxygen maintains life of the living thing through respiration. On the other hand, it is known that oxygen is a very reactive compound so that it reacts with various ingredients in food to oxidize or peroxidize the ingredients thereby to not only reduce their commercial value but also form injurious materials in food. It is reported that for example, nutritionally required unsaturated fatty acids such as linoleic acid, linolenic acid, etc., which are contained in foods, are readily peroxidized by oxygen in the air to form peroxidized fatty acids or reactive radicals (free radicals) and at the same time, form carcinogenic substances such as malone dialdehyde, etc. It is also reported that peroxidized lipids formed by peroxidation of unsaturated fatty acid molecules in lipids modify protein or nucleic acid in vivo to cause the living body in its carcinogenic action, etc. ("Mutagen and Toxicity", vol. 5, page 243 (1982), "Packaging of Food", vol. 17, page 106 (1986)).

In order to prevent such peroxidation of lipids, techniques for packaging such as removal of oxygen in the package with a free oxygen absorber, vacuum packaging, nitrogen gas substitution packaging, etc. have been used. On the other hand, synthetic antioxidants, for example, butylhydroxyanisole (BHA), butylhydroxytoluene (BHT), etc. have been generally used, backed by development of chemical industries. However, as use of such synthetic antioxidants increases, food pollution increases and a serious problem occurs in view of safety. It is thus the actual situation that the consumer's rejection against synthetic antioxidants has been increasing and its amount of use decreases.

On the other hand, it is considered that peroxides or carcinogenes formed in animal living body would adversely affect animal cells due to the toxic action of oxygen as described above. Such peroxidation of vital components with oxygen would be correlated to aging of cells and thus to a life span (theory of free radical aging). Therefore, highly safe antioxidants derived from the natural world have been greatly expected to be substances for supporting the antioxidative protective mechanism in vivo, not only in foodstuffs, especially health maintaining foods or nutrient foods, but also in the technical fields of medicines and cosmetics.

However, the only natural antioxidants that have been expected to be practically used in place of synthetic antioxidant involving problems in food pollution are vitamin C prepared by chemical synthesis and vitamin E (tocopherol) extracted and purified from natural products.

In order to suitably use such antioxidants derived from the natural world for use in foods, drugs, cosmetics, etc., it is important to find natural antioxidants having different properties and utilize the antioxidants under such conditions that their characteristics are exhibited.

A variety of compounds having an antioxidative activity are contained in spices derived from plants and, spices have been added to food as having an action of preserving foods (Packaging of Food, vol. 19, No. 1, page 97, 1987). However, most of spices exhibit a strong flavor or color. In order to add these spices to foods, drugs, cosmetics, etc. as antioxidants or the like, such properties have automatically limited their use range.

Vitamin C is insoluble in fat or lipids in vivo since it is a water soluble substance. On the other hand, vitamin E is insoluble in an aqueous solution such as blood, etc. and accumulated in lipids in vivo, since it is fat-soluble. Such properties of extreme water solubility and fat solubility are not considered to be necessarily advantageous, in the case of foods, drugs, cosmetics, etc. applied to the living body. In order to exhibit their antioxidative activity appropriately in any of lipids and aqueous solutions in vivo, natural substances having an intermediate property between water solubility and fat solubility are advantageous.

In addition to vitamin C or vitamin E, extensive investigations have been made on properties of natural antioxidants derived from spice plants, and reports are made thereon.

However, natural antioxidants other than natural vitamin E, vitamin C, etc., that are expected to be used in place of synthetic antioxidants involving problems in food pollution have not been practically utilized, because their origins are plants or animals affected by natural conditions such as weather, etc. and it is thus difficult to stably supply them, their contents are extremely a trace amount, extraction may be made only with extreme difficulty, and components change during extraction.

A potent antioxidative activity is noted in sesame oil obtained from seeds of Sesamum indicum L. by lignan compounds modified during the course of purification of sesame oil. Thus, sesame oil has been given an important position as an excellent edible oil which is not deteriorated by oxidation ("Grand Modern Encyclopedia", Gakushu Kenkyusha (Jan. 1, 1979), pages 123-124).

On the other hand, it is already known that not only sesame oil is contained in Sesamum indicum L. contains but also antioxidants such as vitamin E or lignan compounds, etc. are contained in the plant body of sesame (Agricultural and Biological Chemistry, vol. 49, page 301 (1985)), Journal of the Japanese Food Industry Association, vol. 32, page 407 (1985)). However, it is quite unknown or not even suggested that growing cells from sesame plants, especially cells grown at a high temperature can be industrially cultivated, a glycoside substance having a potent antioxidative activity is contained in these growing cells, and the substance can be efficiently extracted and produced industrially without causing any denaturation or deterioration.

SUMMARY OF THE INVENTION

The present invention has been made to overcome all the demerits aforementioned. An intensive many-faceted research resulted in the success that a novel antioxidative glycoside represented by the following structural formula (A) can be produced industrially in large quantities and systematically from culture cells prepared by cultivating growing cells (callus) using a synthetic medium, which growing cells are derived from the plant body of sesame (Sasamum indicum L.). Thus the present invention has been completed.

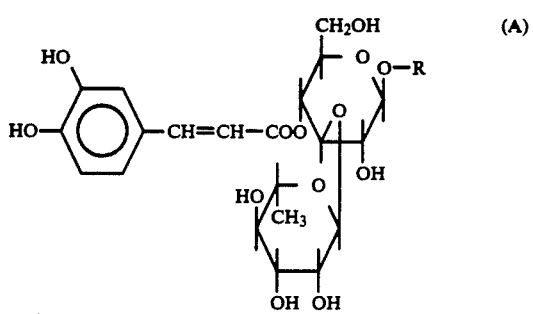

(A)

wherein R is

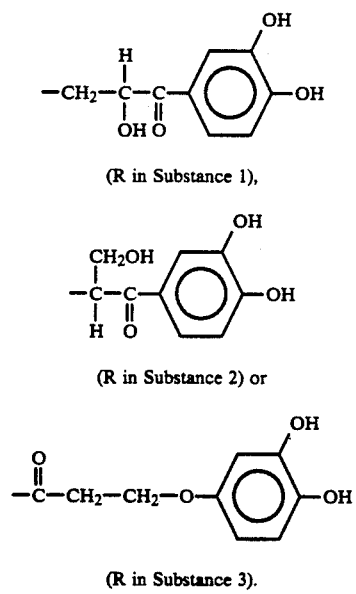

(R in Substance 1), (R in Substance 2) or (R in Substance 3).

Namely, the antioxidative glycoside of formula (A) includes three substances: Substance 1, Substance 2 and Substance 3.

| | | |
|---|---|---|
| ▲ | : | crude extract |
| ● | : | imcompletely purified extract |
| ♦ | : | purified product (Substance 1) |
| □ | : | purified product (Substance 2) |
| ◊ | : | purified product (Substance 3) |
| ⊙ | : | butylhydroxyanisole (BHA) |

Figure 19:
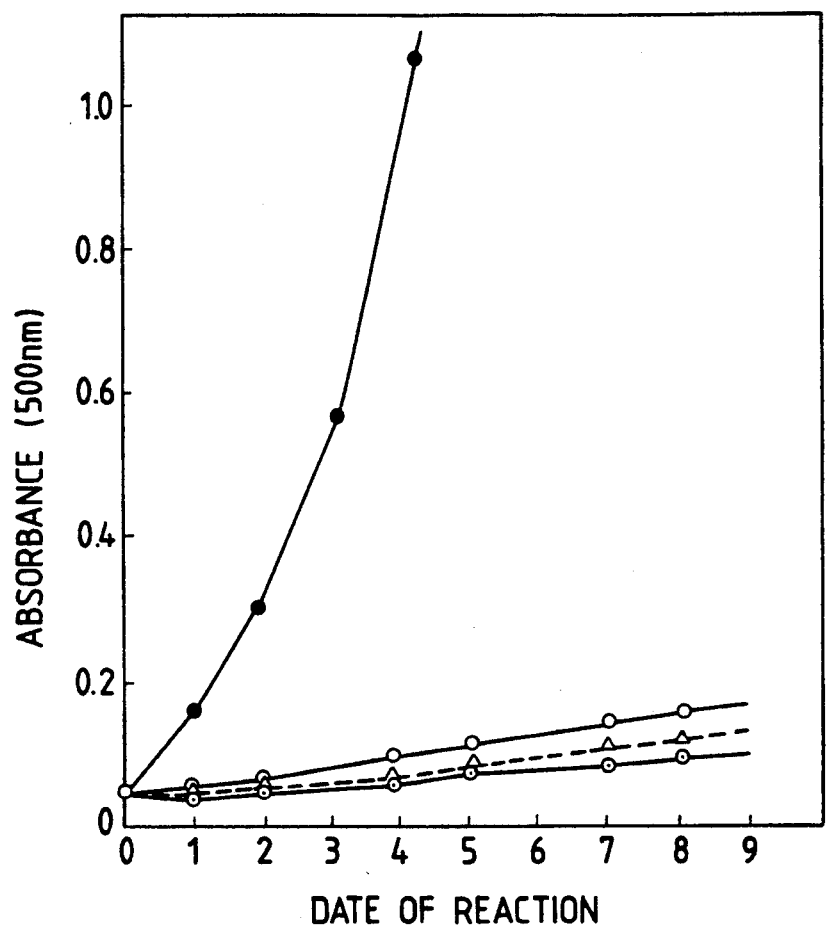

FIG. 19 shows an oxidation curve of linoleic acid, where the procedure of autooxidation was analyzed by the rhodan iron method, using linoleic acid as a reaction substrate.

| | | |
|---|---|---|
| —●— | : | control group |
| —○— | : | α-tocopherol group |
| —△— | : | butylhydroxyanisole group |
| —⊙— | : | crude extract from the sesame cell |

DETAILED DESCRIPTION OF THE INVENTION

The sesame culture cells grown at high temperature which are used in the present invention grow rapidly at a high temperature of 33° to 36° C. and contain large quantities of the antioxidative glycoside therein. Preparation of the cells containing the antioxidative glycoside through culture at such a high temperature is based on the new finding as described above.

Cultivation of the sesame culture cell of the present invention which well grows at a high temperature is described below.

Firstly, a germ, a root or a seed is used as sesame. A seedling is prepared under sterile conditions and a section of the germ, stalk, leaf and/or root is cultured in a solid and/or liquid medium to induce callus cells. The obtained growing callus grows to a big callus by subculture. Then the grown callus is subjected to stationary and/or spinner culture in a solid and/or liquid medium to grow the callus cells.

As the medium, there may be used various media. As carbon sources, there may be also be used polysaccharides such as oligosaccharides, starch, etc., in addition to monosaccharides such as glucose, fructose, etc., disaccharides such as maltose, sucrose, etc. As nitrogen sources, there may be used nitrate type nitrogen such as ammonium nitrate, potassium nitrate, etc., ammonia type nitrogen such as ammonium sulfate, ammonium sulfate, etc., Casamino acid, amino acid, peptone, corn steep liquor, yeast cells, yeast extract, maltose extract, etc.

In addition, there may be used vitamins such as nicotinic acid, nicotinamide, thiamine, folic acid, biotin, etc.; nucleic acid-associated substances such as inositol, adenylic acid, guanylic acid, citidylic acid, thymidylic acid, cyclic AMP, etc.; minerals such as iron, manganese, zinc, boron, iodine, potassium, cobalt, magnesium, molybdenum, phosphorus, copper, etc.

An example of basal medium is shown in Table 1.

TABLE 1

| | |
|---|---|
| Ammonium nitrate | 1,650 mg |
| Potassium nitrate | 1,900 |
| Calcium chloride | 440 |
| Magnesium sulfate | 370 |
| Monopotassium phosphate | 170 |
| Boric acid | 6.2 |
| Manganese sulfate | 22.3 |
| Zinc sulfate | 8.6 |
| Potassium iodide | 0.83 |
| Sodium molybdate | 0.25 |
| Cobalt chloride | 0.025 |
| Copper sulfate | 0.025 |
| Sodium ethylenediaminetetraacetate | 37.3 |
| Ferrous sulfate | 27.8 |
| Myoinositol | 100 |
| Glycine | 2 |
| Pyridoxine hydrochloride | 0.5 |
| Nicotinic acid | 0.5 |
| Thiamine hydrochloride | 0.1 |
| Sucrose | 30 g |
| Water | 1,000 ml |
| pH 5.7 | |

It is preferred to supplement auxin and cytokinin to the basal medium. As the auxin, indoleacetic acid, indolebutyric acid, naphthaleneacetic acid, 2,4-dichlorophenoxyacetic acid, etc. may be appropriately used. As the cytokinin, there may be used benzyladenine, kinetin, etc. These plant hormones or cytokinins may be used singly but the use in combination is effective. The growing callus may be cultured in a medium having the composition shown in Table 1. However, for further improving its growing nature, it is effective to supplement natural organic nutrient sources such as coconut milk, casein hydrolysate, potato extract, corn steep liquor, yeast extract, maltose extract, etc. Culture temperature may be operated between 28° and 37° C. but preferably between 33° and 36° C. It is advantageous for proliferation to set a pH of the culture broth to weakly acidic (pH 5.6 to 6.0).

In order to cultivate the stably growing cells from the thus obtained sesame callus cells, a small mass of the cells are transplanted to solid plate medium solidified with gellan gum or agar and cultured for 1 to 2 weeks under growth conditions later described. In this case, it is preferred to maintain the culture temperature at 33° to 36° C.

The cell line having a high growing property is selected from many cell lines of high density culture cells. A large number of small cell masses are taken out of the cell population and transplanted to a fresh medium thereby to construct a larger number of the cell lines. By repeating subculture of such cell lines 5 to 10 times at a high temperature of 33° to 36° C., sesame culture cells capable of stably growing at a high temperature are cultivated.

To extract the antioxidant from the growing cells obtained by cultivation, the antioxidant may be recovered by destructing the cells by a biological treatment using cellulase or lysozyme, a chemical treatment, a mechanical treatment or ultrasonication, or a combination thereof, and then extracting the antioxidant with methanol, ethanol, acetone, chloroform or other organic solvent, water, or the like, singly or as admixture of these organic solvents and water.

The activity of the antioxidant may be assayed by determining an automatic oxidation amount of linoleic acid as a reaction substrate with air according to the rhodan iron method. This is a conventional method used to examine peroxidation of lipid (Agricultural and Biological Chemistry, 45, 735 (1981)).

Next, collection of sesame culture cells which are cultivated according to the present invention and can grow at a high temperature is described in detail, with reference to experimental steps.

1. Preparation of Sesame Seedling Aseptically Grown

After thoroughly washing with water, sesame seeds are immersed in 75% ethanol aqueous solution for several seconds. The seeds are then washed with sterile water separately prepared and then immersed in 0.1% benzalkonium chloride (commercially available sterilizer) for 2 to 5 minutes to sterilize microorganism adhered to the seeds. After thoroughly washing again with sterile water, the seeds are treated with 1% sodium hypochlorite (manufactured by Wako Pure Chemicals) sterilizer solution (containing 0.1% surfactant, Tween 20) for 30 minutes to completely sterilize the sesame seeds.

On the other hand, a sterilized wide-mouthed bottle with a cover (plastic-made, commercially available) is prepared. Basal medium having a composition shown in Table 1 (provided that no sucrose was added; 0.8 to 1.5% of a solidifying agent is added in the case of agar and 0.2 to 0.3% was added in the case of gellan gum) is separately sterilized in an autoclave and poured into the wide-mouthed bottle to solidify and used as solid medium for seeding. Alternatively, sterile water and sterile gauze are aseptically put in a wide-mouthed bottle, which may be used as a seeding bed. The sterilized sesame seeds are seeded on such a medium or bed for seeding by aseptic operation. When the medium or bed is kept at 28° to 30° C. in a temperature controlled room under light of a fluorescent lamp, the sterilized sesame seeds seedle without being perished. Thus, sesame seedlings of 3 to 5 cm long may be prepared in about 10 days. The seedlings are in a completely sterilized state and utilized for cultivation of growing cells.

2. Induction Culture of Growing Cell Mass Derived from Sesame

Media having various composition are prepared by adding naphthaleneacetic acid ($10^{-8}$ to $10^{-5}$M) or 2,4-dichlorophenoxyacetic acid ($10^{-8}$ to $10^{-5}$M) as auxin; benzyladenine ($10^{-6}$ to $10^{-4}$M) or kinetin ($10^{-6}$ to $10^{-4}$M) as cytokinin, in combination, to basal medium having the composition shown in Table 1. As a solidifying agent 0.2% of gellan gum or 0.8% of agar is added to the medium and a pH is adjusted to 5.7. Then the medium is separately charged and solidified in a Petri dish conventionally used for incubation of a microorganism. A section of the sesame seedling aseptically prepared as described above is transplanted to the medium and cultured in a temperature controlled room or box at 28° to 30° C. in the dark. Two to three weeks after the culture, the cells grow from the section of the sesame seedling to a mass to form callus. By subculturing the growing callus in medium having the same composition, a large callus can be cultivated.

As the basal medium used for artificial induction of callus, the medium composition (Murashige-Skoog's medium) shown in Table 1 was used. However, any medium is usable so long as it is conventionally used for plant cell culture. Basic composition of such medium is well known in the art (Manual of Plant Cell Culture, published by KODANSHA (1984)).

3. Cultivation of Callus Cells

The growing cell mass (callus) induced from sesame seedling is cultivated into stably growing cells in a sterile, solidified medium obtained by supplementing auxin or cytokinin such as naphthaleneacetic acid (1 to $5 \times 10^{-5}$M), benzyladenine (1 to $5 \times 10^{-5}$M), etc. to the medium having the composition shown in Table 1 and further adding thereto 0.2% of gellan gum or 0.8% of agar as a solidifying agent.

Sesame cells well grow in the dark but grow more actively in the light. It is thus observed that sesame cells well grow in the light of 3,000 to 30,000 lux, preferably 8,000 to 15,000 lux. The sesame cells may grow at a temperature of 30° to 37° C. but are cultured preferably at 33° to 36° C.

In order to cultivate cells capable of stably growing at a high temperature from the sesame callus, a small mass of the cells are transplanted to solid plate medium obtained using gellan gum or agar followed by culturing for 1 to 2 weeks under the growth conditions described above.

The culture temperature in this case is set at a temperature higher than that used for induction culture of callus cells. That is, the culture temperature is maintained at 33° to 36° C., whereby the cells vigorously grown can be concentrated.

From many cell lines thus obtained, the cell line which grow vigorously is selected and many small cell masses are taken out of the cell population. The small masses are transplanted to a fresh medium to prepare many cell lines. By repeating subculture of these cell lines 5 to 10 times, sesame cells which can stably grow at a high temperature of 33° to 36° C. are cultivated.

4. Culture of Growing Cells

For cultivation of sesame cells capable of stable subculture, a medium having the composition shown in Table 1 is used but media having compositions conventionally used for culturing plant cells may also be utilized. In such a basal medium, naphthaleneacetic acid (1 to $5 \times 10^{-5}$M) and benzyladenine (1 to $5 \times 10^{-5}$M) are formulated as auxin and cytokinin, respectively. In the case of liquid culture, the medium may be used for growth culture as it is but in the case of culturing in a solid medium, 0.2% of gellan gum or 0.8% of agar is added to the medium, sterilized and solidified for use. It is advantageous for the cell growth to irradiate the cells with light. Irradiation may be performed with generally 3,000 to 30,000 lux, preferably 8,000 to 15,000 lux. The cells grow at a temperature of 28° to 37° C., preferably 33° to 36° C. For liquid culture, shake culture or aerial spinner culture which is used for culturing ordinary microorganism is adopted, but is preferably operated under milder conditions than in culturing microorganism. An amount of oxygen required may be extremely smaller than that required for culturing microorganism. It is thus preferred for cell growth to stir to such a degree that the cells do not deposit at the bottom of culture broth, while airing slightly.

For more effective growth culture, it is preferred to maintain a pH of the culture broth at 5.6 to 5.8.

In ordinary growth culture, incubation is completed in 1 to 2 weeks. It is thus possible to recover the cells from the culture broth in a conventional manner such as centrifugation, etc. In the case of solid culture, the proliferated cell mass may be readily recovered.

Thus, sesame cells capable of producing in an industrial scale are cultivated and proliferated in large quantities.

Figure 1:
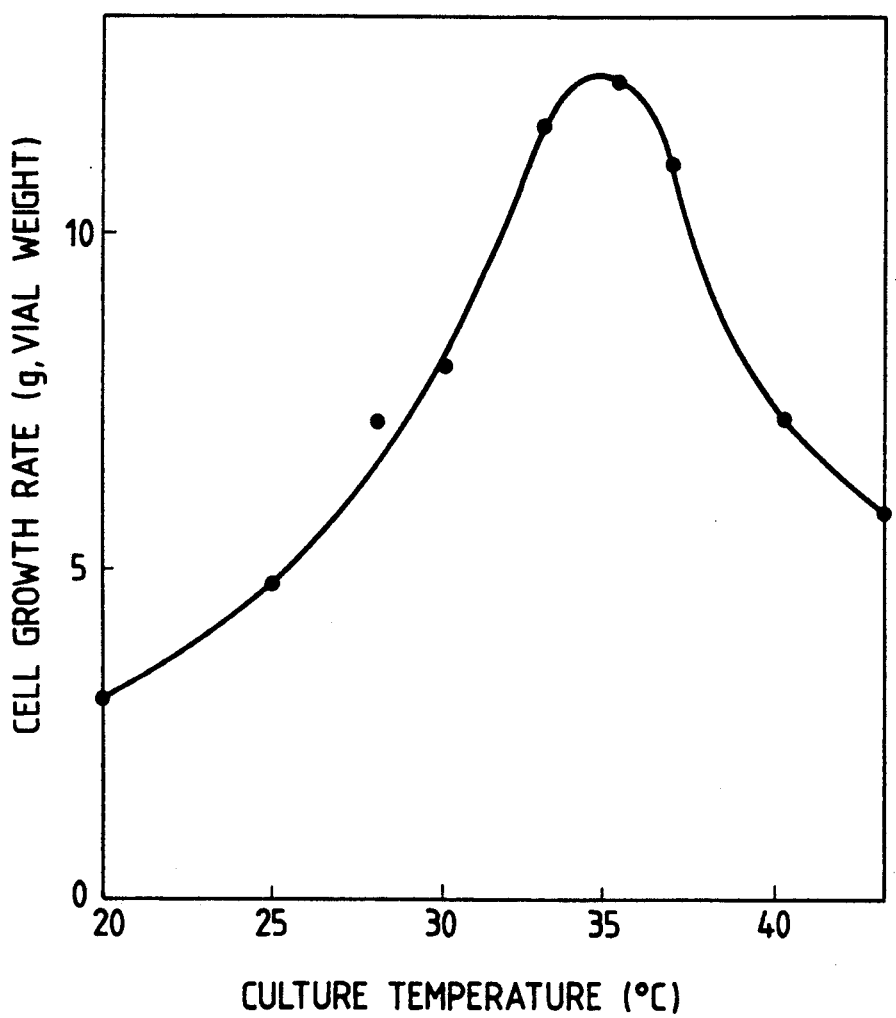
FIG. 1 is a graph showing relationship between a growth rate of callus cultured at a high temperature and a culture temperature.
Figure 2:
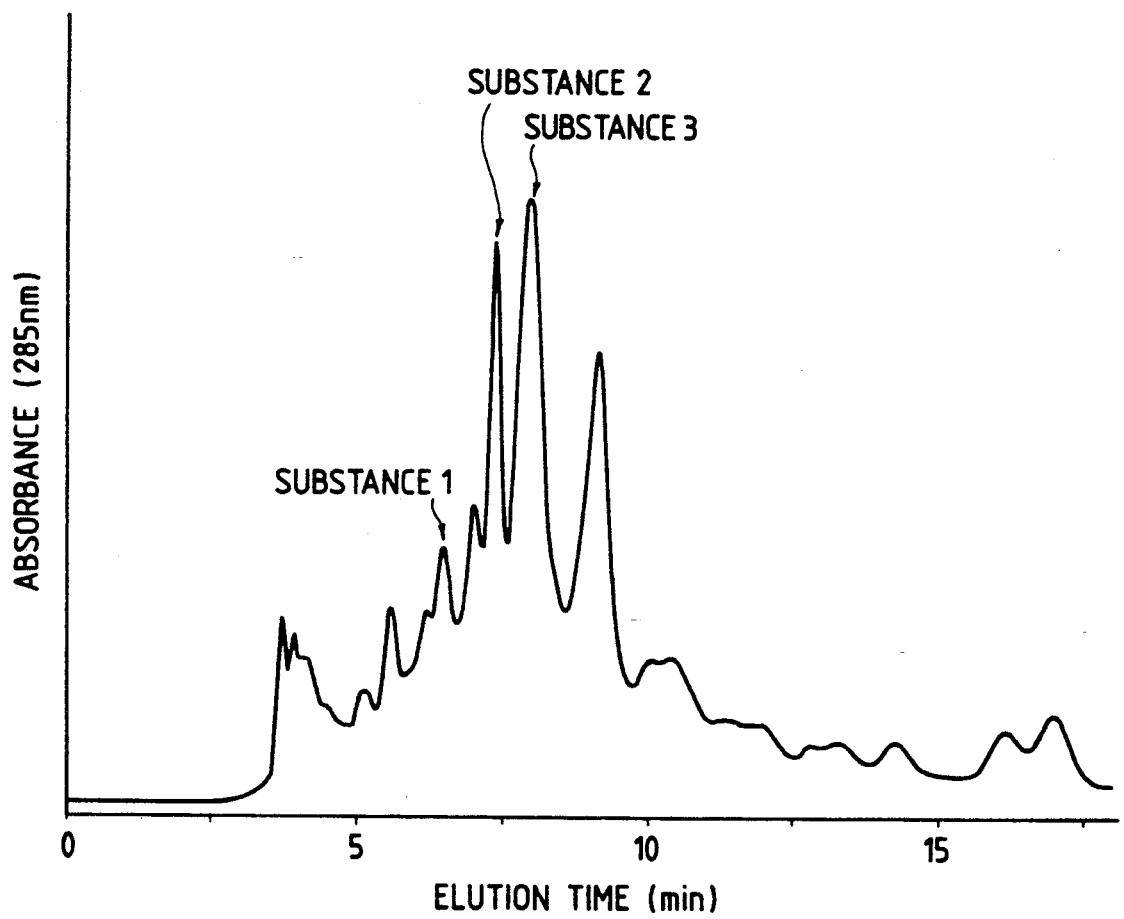
FIG. 2 is a chromatogram of the incompletely purified extract by liquid chromatography, showing a composition of components contained in the incompletely purified extract eluted by adsorption chromatography.
Figure 3:
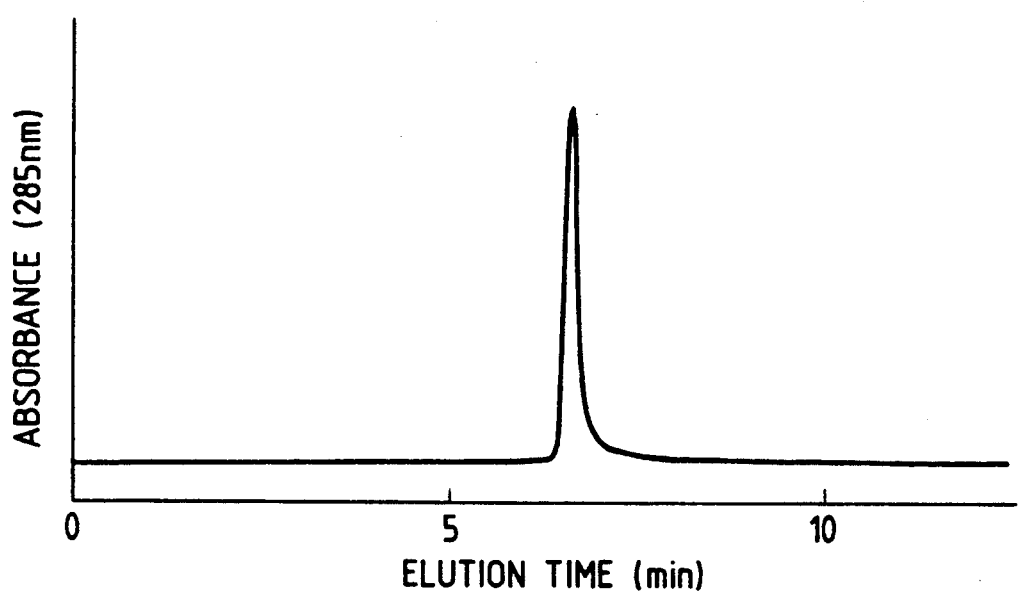
FIGS. 3, 4 and 5 show each chromatogram of Substances 1, 2 and 3 purified by liquid chromatography, respectively.
Figure 4:
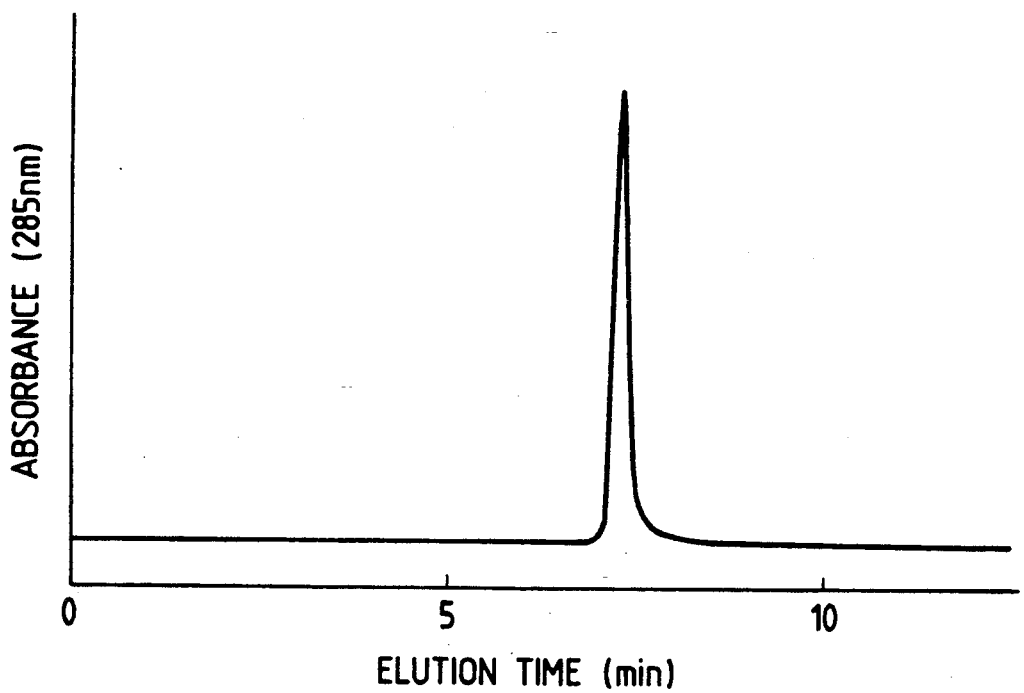
Figure 5:
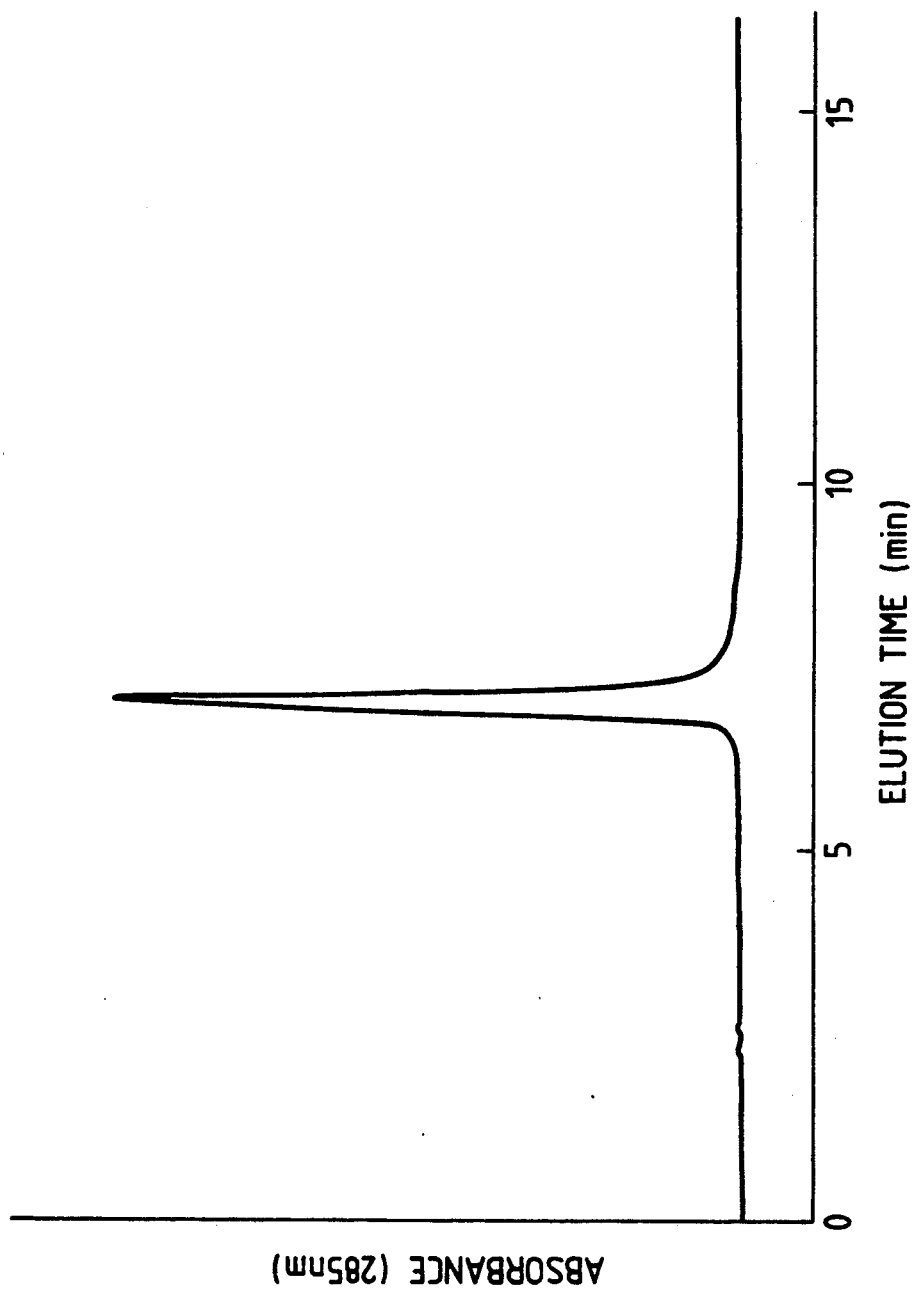
Figure 6:
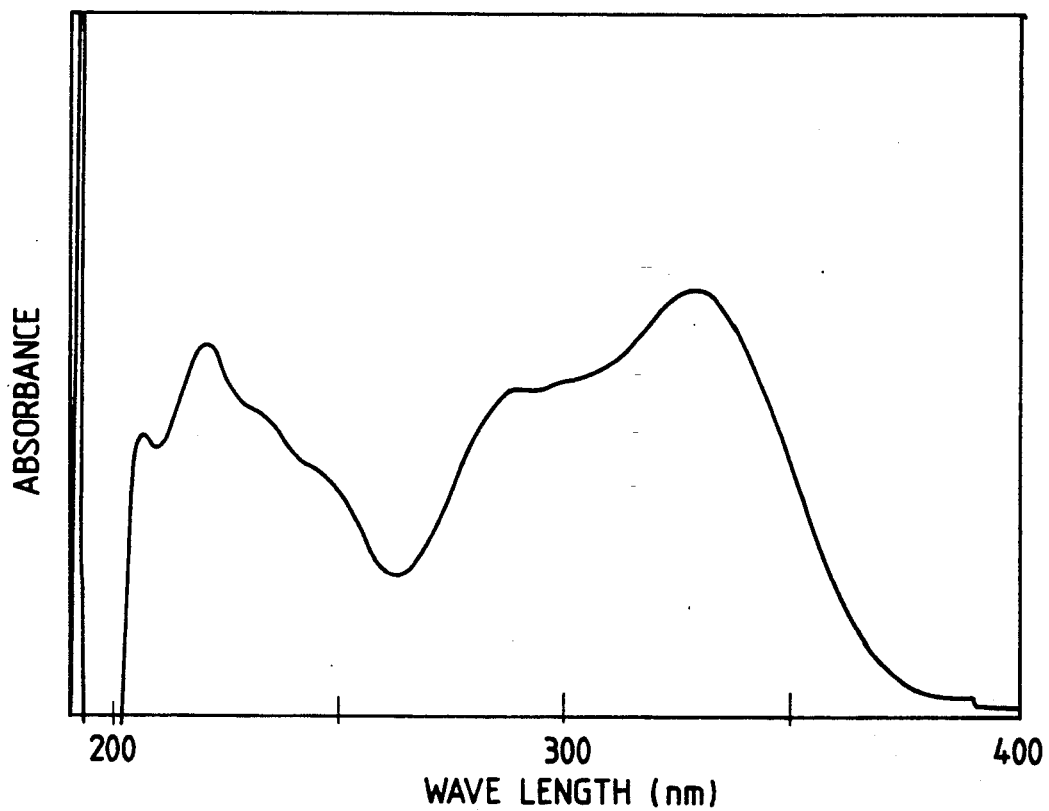
FIGS. 6, 7 and 8 are each UV absorption spectrum of Substances 1, 2 and 3, respectively.
Figure 7:
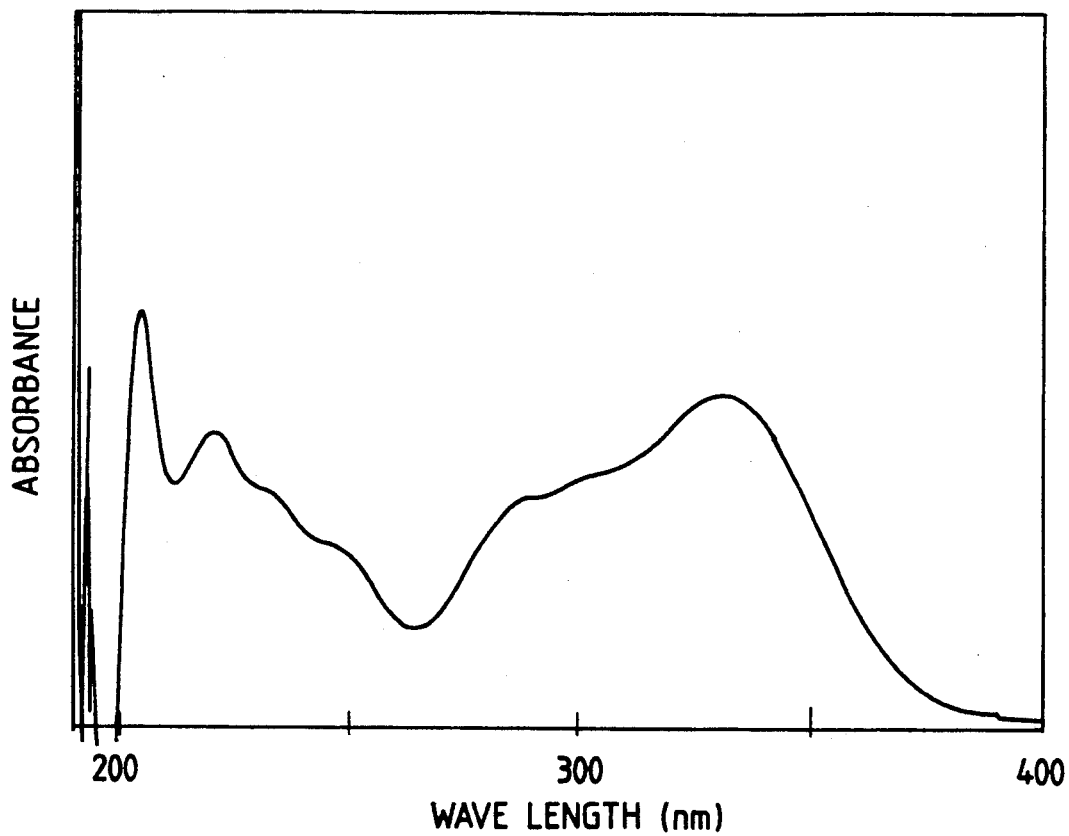
Figure 8:
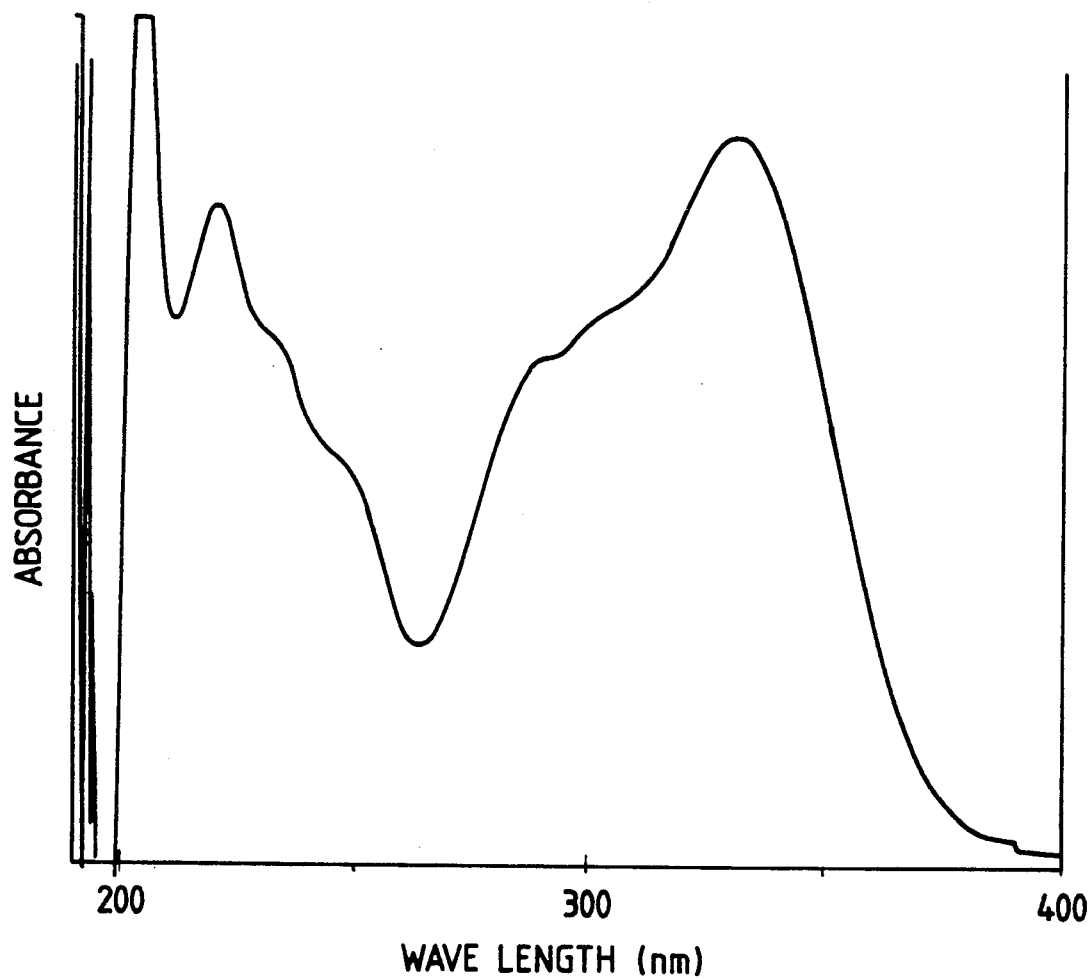
Figure 9:
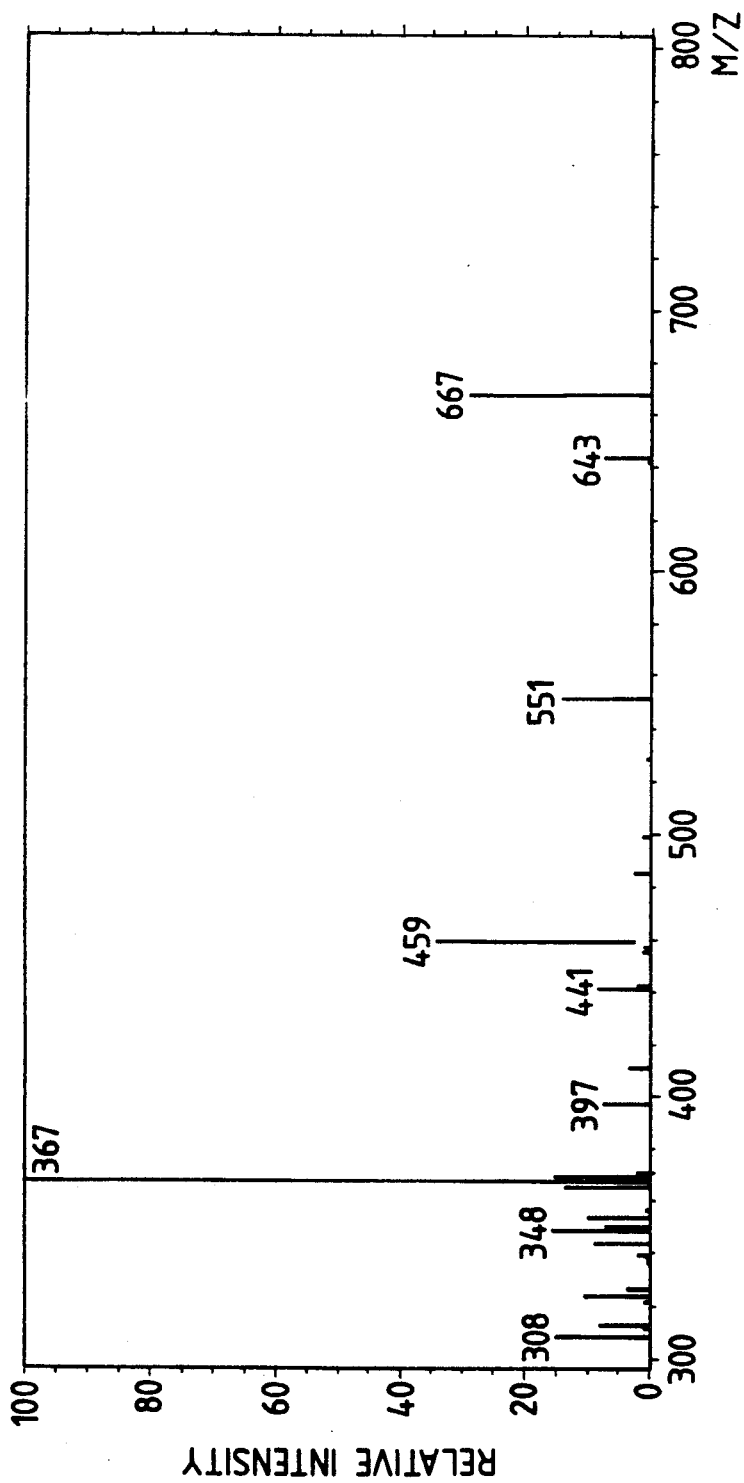
FIGS. 9, 10 and 11 are each analytical pattern of Substances 1, 2 and 3 by high speed electron bombardment mass spectrum, respectively.
Figure 10:
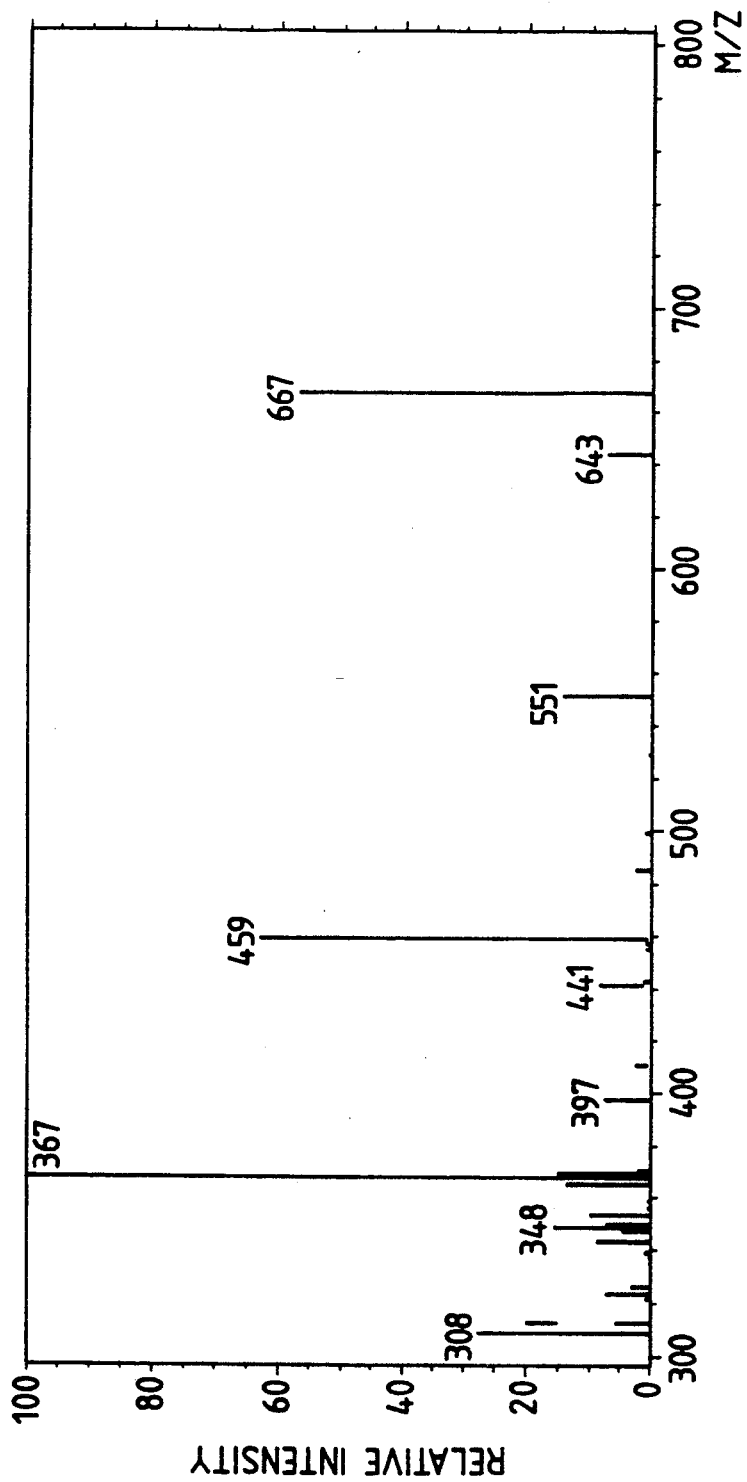
Figure 11:
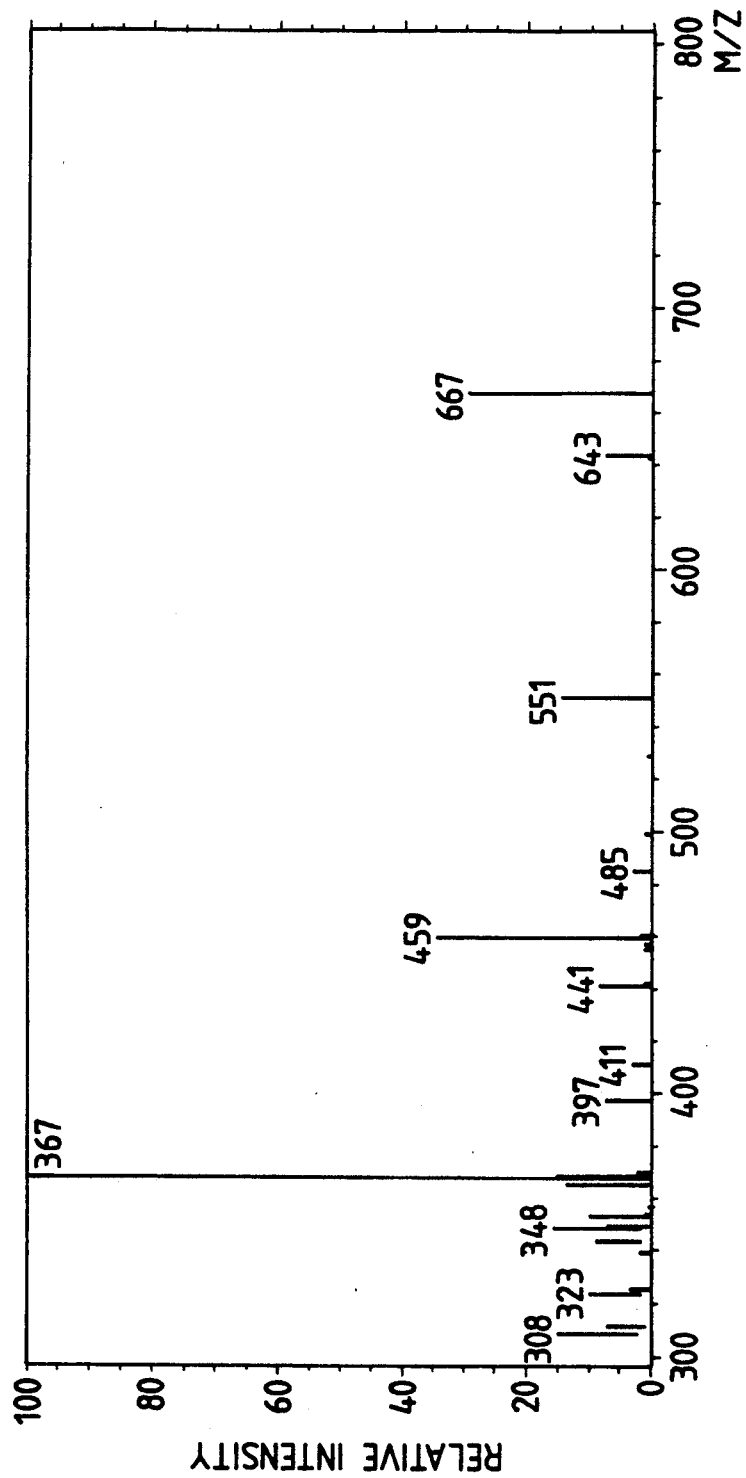
Figure 12:
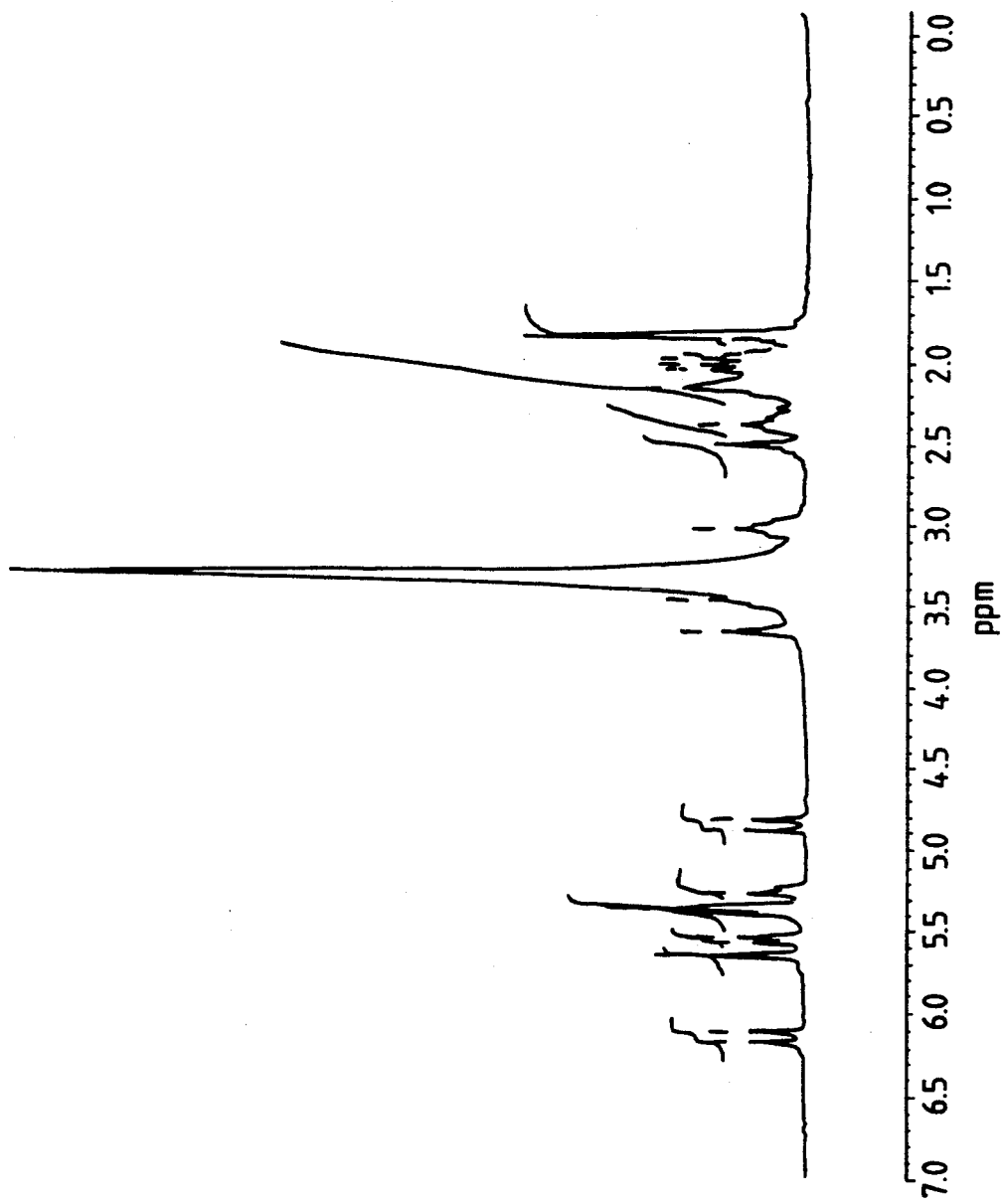
FIGS. 12, 13 and 14 are each spectrum of Substances 1, 2 and 3 by protonic nuclear magnetic resonance ($^1$H-NMR), respectively.
Figure 13:
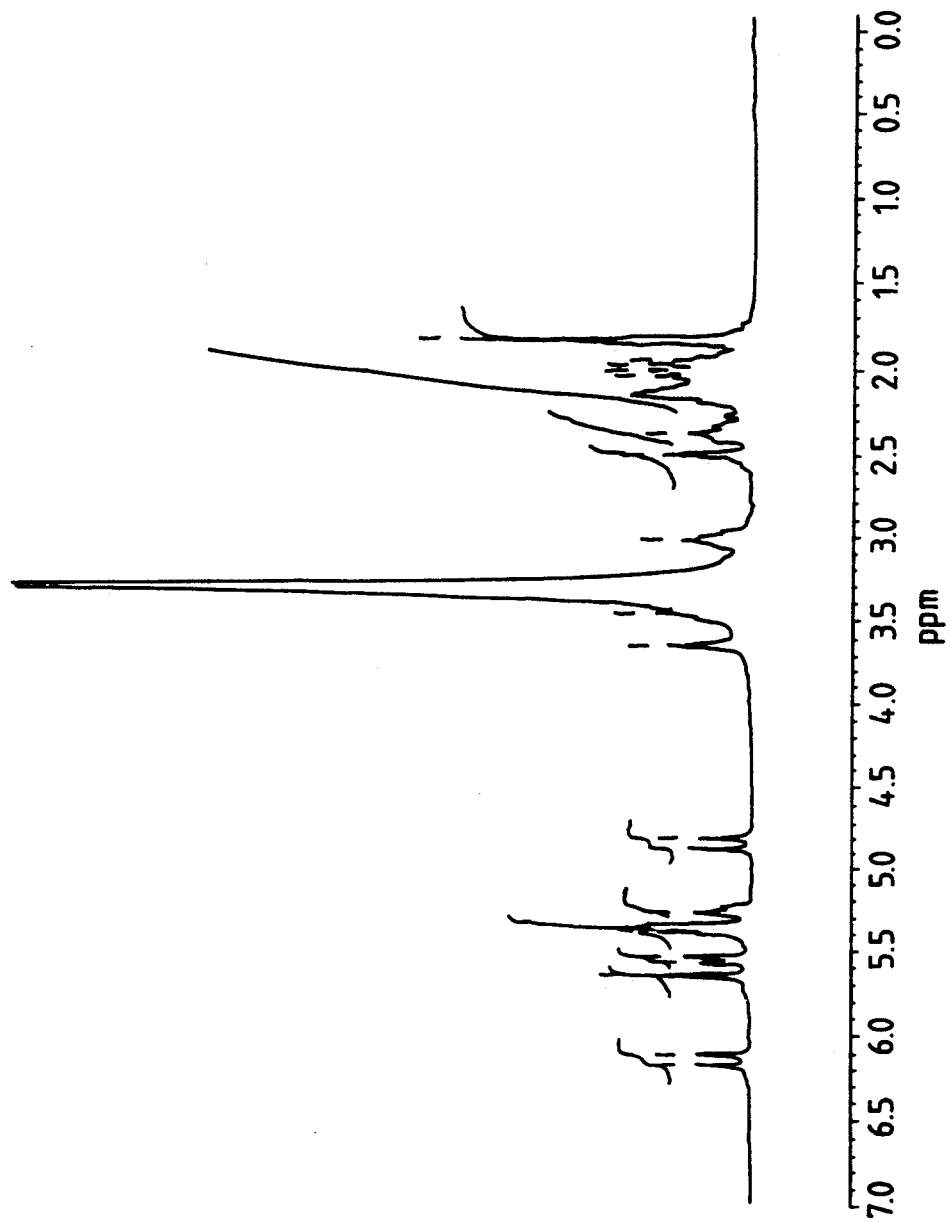
Figure 14:
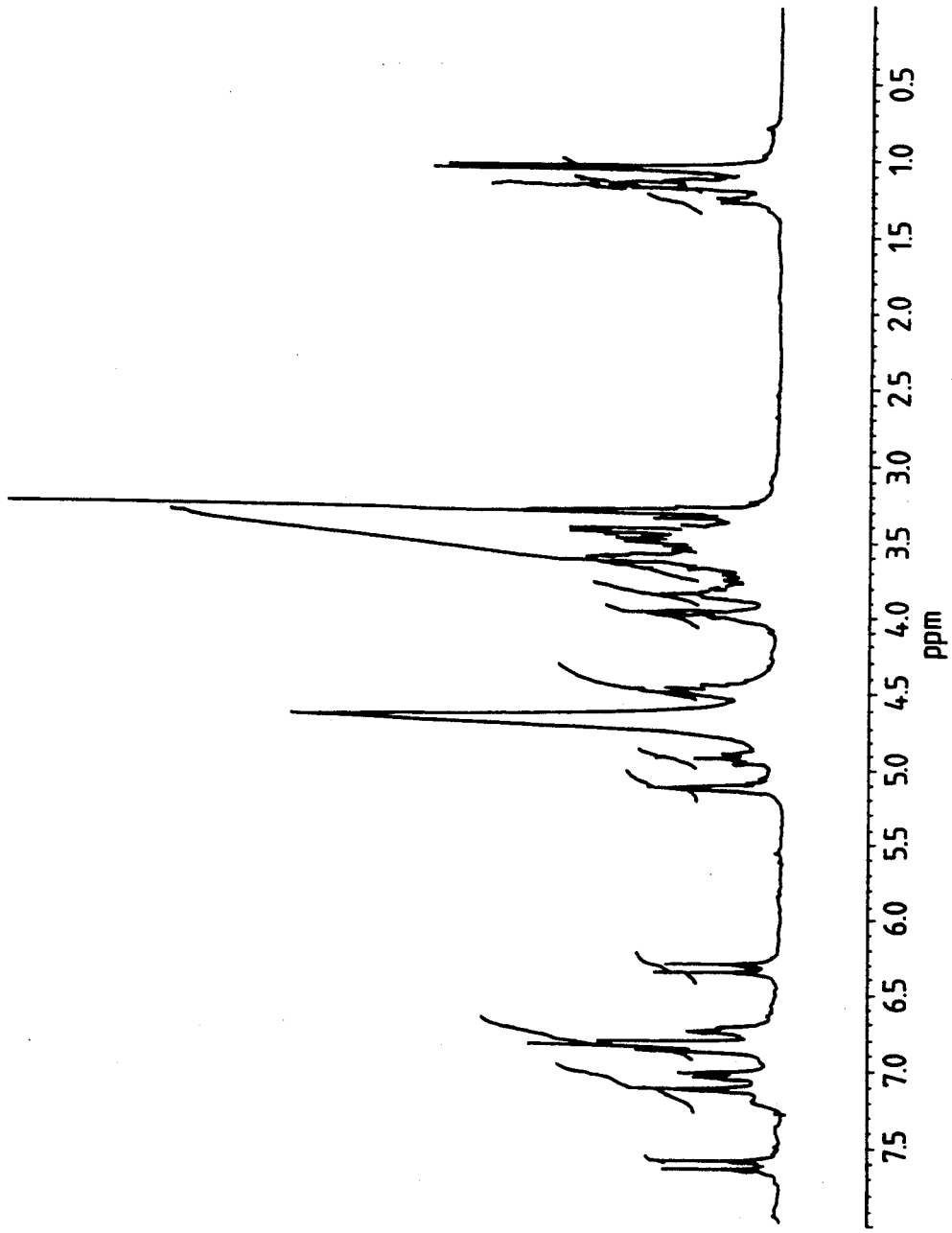
Figure 15:
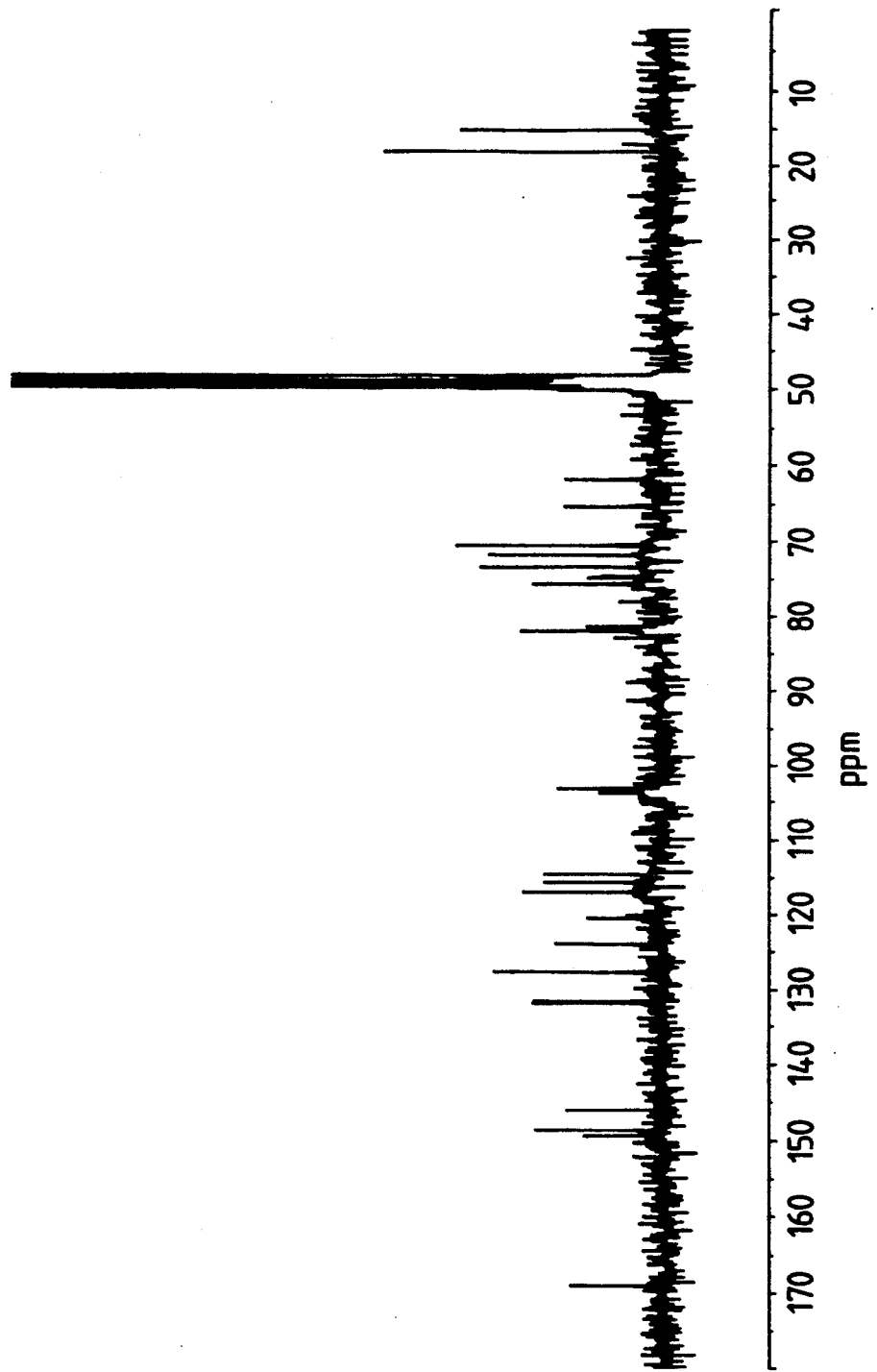
FIGS. 15, 16 and 17 are each spectrum of Substances 1, 2 and 3 by carbon 13 nuclear magnetic resonance ($^{13}$C-NMR), respectively.
Figure 16:
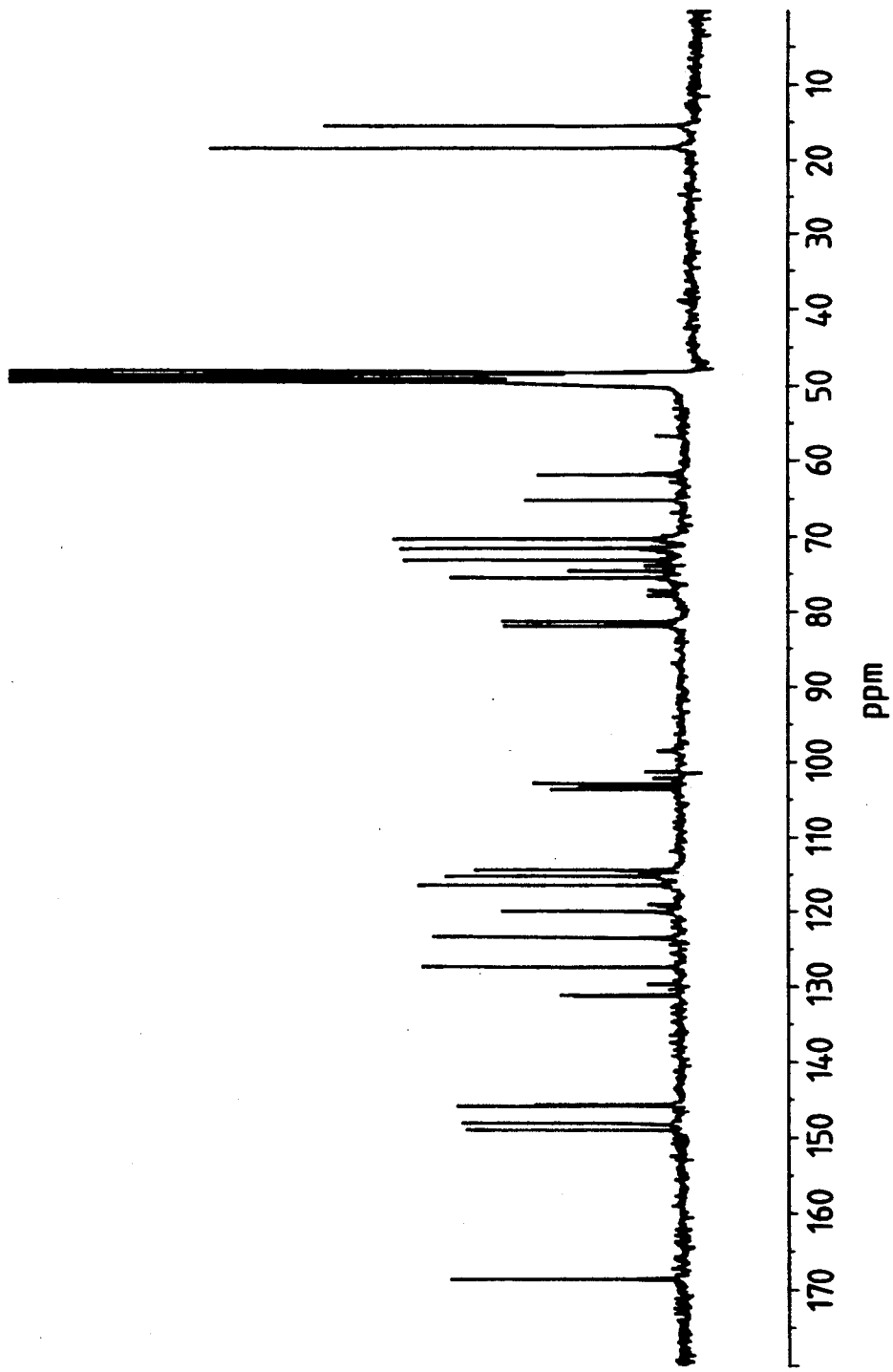
Figure 17:
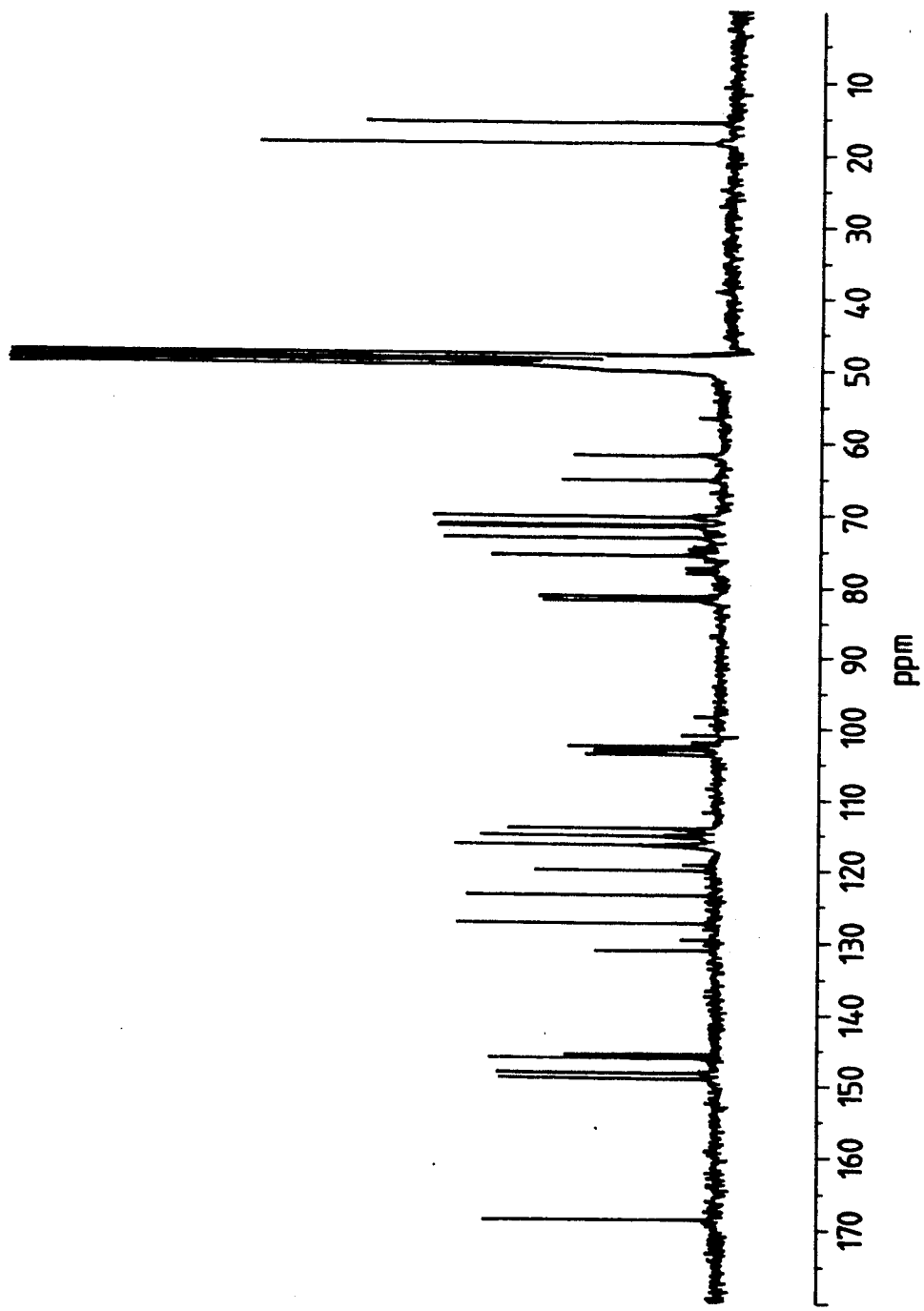
Figure 18:
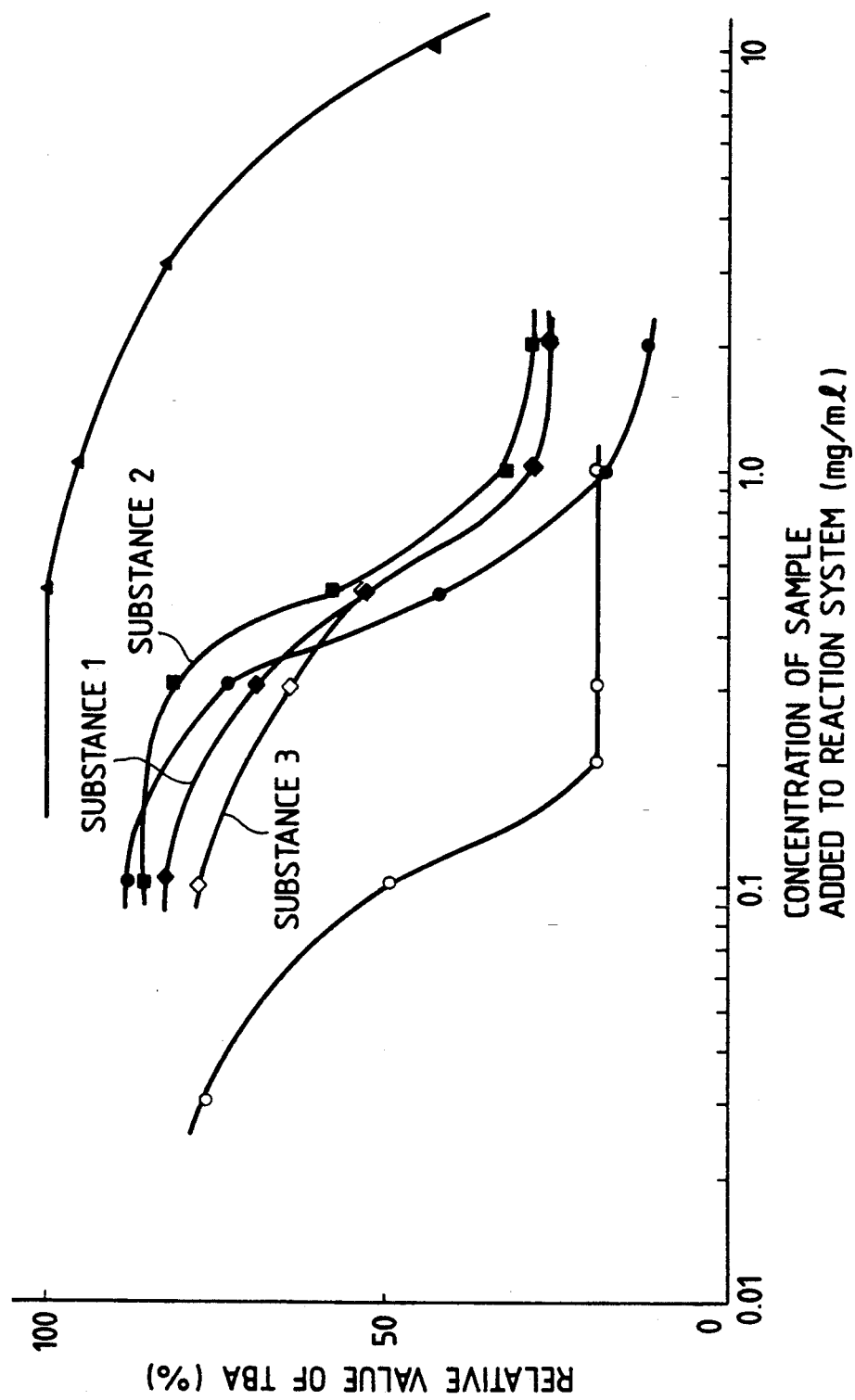
FIG. 18 shows an antioxidative activity of the crude extract from sesame culture cells by the rabbit erythrocyte membrane ghost method, the incompletely purified extract (intermediary product) and purified products (Substances 1, 2 and 3).

FIG. 1 shows relationship between a growth rate of the thus obtained sesame culture cells grown at a high temperature and culture temperature. The growth rate at 35° to 36° C. is about twice or more than that at a temperature of 25° to 28° C. which is generally used for culturing plant cells. The growth speed is also fast. Therefore, the sesame culture cells may be effectively used in culturing plant cells industrially.

5. Extract of Antioxidant and its Assay

The growing callus cells obtained as described above is broken into fine pieces with a blender, etc. and then macerated together with quartz sand. The macerated cells are extracted with a solvent such as methanol, etc., dehydrated with anhydrous sodium sulfate and evaporated to dryness at 30° to 35° C. The residue is again dissolved in methanol to give a fraction containing the antioxidant.

Next, a method for assaying the antioxidative activity is described. The method comprises using linoleic acid as a reaction substrate and utilizing the rhodan iron method often used to determine the degree of oxidation of oils and fats. That is, the method comprises oxidizing divalent iron ions to trivalent iron ions with peroxides formed by autoxidation of oils and fats; reacting the trivalent iron ions with ammonium thiocyanate to form red rhodan iron; and measuring absorbance of the rhodan iron, whereby an amount of the peroxides of oils and fats is determined (Agricultural and Biological Chemistry, 45, 735 (1981)).

Furthermore, the so called erythrocyte membrane ghost method utilizing peroxidation of rabbit erythrocyte membrane lipid was also used as a method for assay, which is closer to the in vivo system, than in the rhodan iron method.

From a rabbit blood cell, its membrane alone is prepared and called erythrocyte membrane ghost.

After t-butylhydroxy peroxide is added to the erythrocyte membrane ghost as an initiator of oxidation of accelerate peroxidation of phospholipid in the erythrocyte membrane, the formed malonedialdehyde (strongly carcinogenic substance) or its analog is reacted with thiobarbituric acid to form a color and its absorbance is measured (Biochemistry, 78, 6858 (1981)).

In any of the methods, a degree of the color formed with thiobarbituric acid changes in association with the degree of antioxidative activity in the sample added to the reaction system. Thus, by contrasting with the control group containing no antioxidant, the antioxidative activity in the sample can be determined.

6. Extract, isolation and structural analysis of antioxidative glycoside

The cells grown by liquid culture may be readily recovered by gravity fractionation or centrifugation. Ethyl alcohol is added to the thus obtained cells in a final concentration of 80%. The antioxidative glycoside is extracted from the mixture with a mechanically stirring homogenizer. After the extract is recovered by centrifugation, the remained cells are again extracted with 80% ethyl alcohol. The resulting extract is concentrated under reduced pressure and the concentrate is evaporated to dryness to give the syrup-like, yellowish brown crude extract of antioxidant.

The crude extract is subjected to adsorption chromatography using, e.g., Amberlite XAD-II to adsorb the antioxidant onto the resin, which is then eluted with a solvent mixture of water and methanol to give the fraction having antioxidative activity. The fraction eluted with 60% methanol aqueous solution is collected and concentrated under reduced pressure to give representative components of the antioxidant contained in the sesame culture cells.

By isolation and assay of the components by means of high performance liquid chromatography conventionally used in the field of natural chemistry, the degree of purification of the desired components is determined. High performance liquid chromatogram of the fraction eluted from the alcohol extract of sesame culture cells with 60% methanol aqueous solution by adsorption chromatography gives many peaks. From peaks having a potent antioxidative activity, the three glycosides of the present invention were obtained.

By using methods for the structural analysis of natural matters, the structural formula of the glycoside of the present invention was determined to be the following formula (A):

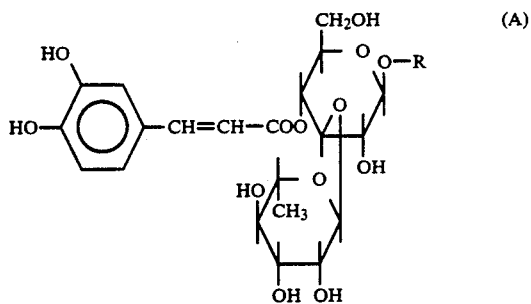

(A)

wherein R is

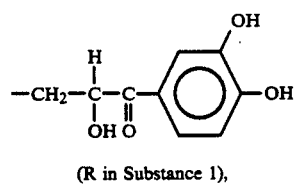

(R in Substance 1),

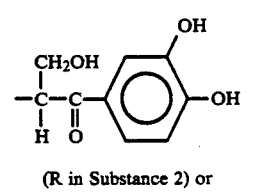

(R in Substance 2) or

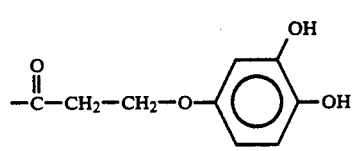

-continued
(R is Substance 3).

Substances 1, 2 and 3 obtained in Example 2 belowmentioned were used to determine their structural formulae.

Where the glycoside having formula (A) is industrially used as the antioxidant, it is advantageous to use Substance 1, 2 or 3 each alone, or a crude or purified mixture of two or three of these (Substances 1, 2 and 3), depending upon purpose. There is no substantial difference in antioxidative activity between the product purified and the incompletely purified product (intermediary product) obtained by adsorption chromatography. Strictly speaking, it is considered that the antioxidative activity would be appreciated also in the components other than the glycoside of formula (A) which are contained in the intermediary product, or the co-present substances would have an accelerating action (synergistic action) of antioxidative activity. This sufficiently suggests that the crude product would be usable.

Furthermore, the fact that the substance has a glycoside structure indicates the characteristic inbetween water solubility and fat solubility. Use range of the antioxidant is broadened, as compared to water-soluble vitamin C, fat-soluble vitamin E, butylhydroxyanisole (BHA), butylhydroxytoluene (BHT), etc. Also in vivo activity, its advantage is greatly expected.

Hereinafter the present invention is illustratively described with reference to the examples and test examples, but is not deemed to be limited thereto.

Each cell relating to the present invention can be readily obtained by using ordinary sesame plant and treating the sesame plant body according to the procedures described above and the procedures of the examples later described. It was confirmed that they are sufficiently reproductive. The starting material is readily accessible without any difficulty and its treatment involves no particular difficulty. Therefore, anyone can make easy access to the cells in accordance with the present invention.

EXAMPLE 1

(1) Seeds of sesame (*Sesamum indicum* L.) prepared were immersed in 75% ethanol for several seconds followed by washing twice with sterile distilled water. The seeds were then immersed in 0.1% benzalkonium chloride solution (manufactured by Amakasu Chemical Industry Co., Ltd.) for 2 minutes. After thoroughly washing 3 times with sterile distilled water, the seeds were immersed in a sterilizer solution containing 1% sodium hypochlorite (Wako Pure Chemicals) and 0.1% Tween 20 (Wako Pure Chemicals) for 30 minutes. After washing with sterile water, sterilized sesame seeds were prepared.

Sterile water and sterile gauze were put in a plastic container (manufactured by Flow Laboratories Co., Ltd.) for plant culture and the previously sterilized sesame seeds were seeded thereon. The seeds were allowed to stand for 2 weeks under a fluorescent light of 20W in a temperature controlled room at 30° C. Seedlings of 5 to 7 cm long were thus obtained.

(2) Two liters of medium having the composition shown in Table 1 were prepared and 100 ml of each aliquot was supplemented with 0.2% of gellan gum (manufactured by San-Ei Chemical Industry) and cytokinin and auxin under the experimental conditions as shown in Table 2, which were made induction media of growing cell mass (callus). These media were sterilized in an autoclave at 120° C. for 15 minutes.

These media were separately charged in 3 each of Petri dish having a diameter of 10 cm by 30 ml each and solidified at room temperature.

The sesame seedlings prepared in (1) were cut at the stalk and leaves into sections of 5 to 7 mm by aseptic operation and transplanted to the solid media in Petri dishes. In order to prevent moisture from being evaporated, sealing was made with Parafilm (manufactured by American Can Co., Ltd.). By allowing to stand in a temperature controlled room of 28° to 30° C. in the dark for 3 weeks, callus was induced from the sections of sesame seedlings. The results are shown in Table 2.

TABLE 2

| Cytokinin | Auxin | State of Callus Induction |
|---|---|---|
| Benzyladenine | Naphthaleneacetic acid | |
| $1 \times 10^{-5}$ M | $5 \times 10^{-5}$ M | ++++ |
| | 1 | +++ |
| | 0.1 | ++ |
| | 0.01 | − |
| | 2,4-Dichlorophenoxyacetic acid | |
| | $5 \times 10^{-5}$ M | − |
| | 1 | + |
| | 0.1 | ++ |
| | 0.01 | ++++ |
| Kinetin | Naphthaleneacetic acid | |
| $1 \times 10^{-5}$ M | $5 \times 10^{-5}$ M | ++++ |
| | 1 | ++++ |
| | 0.1 | +++ |
| | 0.01 | − |
| | 2,4-Dichlorophenoxyacetic acid | |
| | $5 \times 10^{-5}$ M | + |
| | 1 | + |
| | 0.1 | +++ |
| | 0.01 | ++++ |

+: amount of callus induced; the larger the number of symbol +, the better the results
−: no callus induction (3) After adding 0.2% gellan gum, $5 \times 10^{-5}$M of naphthaleneacetic acid and $1 \times 10^{-5}$M of benzyladenine to basal medium having the composition of Table 1, 600 ml of medium was sterilized and prepared in a manner similar to (1). The medium was separately charged in 20 plastic Petri dishes by 30 ml each and solidified. The growing callus obtained by induction culture in (1) was transplanted to Petri dish by 4 each per dish. Culture was performed at 33° to 36° C. for 2 weeks in a plant cell culture device under light of 12,000 lux. The cell mass showing a good growth property was selected and made seed cells. Subculture of the seed cells was repeated 4 times at 33° to 36° C. Thus, the culture cells capable of stably growing at a high temperature were cultivated. The thus-obtained cell culture was named $N_5B_5S$-HT (sesame culture cells subcultured with $5 \times 10^{-5}$M of naphthaleneacetic acid and $1 \times 10^{-5}$M of benzyladenine).

(4) After adding 0.2% gellan gum, $5 \times 10^{-5}$M of naphthaleneacetic acid and $1 \times 10^{-5}$M of benzyladenine to basal medium having the composition of Table 1, 1 liter of the medium was sterilized and prepared in a manner similar to (1). The medium was separately charged in a glass container for plant cell culture having a diameter of 4 cm and depth of 13 cm by 40 ml each and then solidified. A 5-7 mm section of sesame growing cell line $N_5B_5S$-HT cultivated in (3) by subculture was transplanted and cultured at 35° to 36° C. for 10 days in a plant cell culture device under light of 12,000 lux. As the result, the cells grown in the culture container weight 14.5 g in average.

After 60 g of the cells was taken in a mortar, 6 g of quartz sand was added thereto. After maceration for 5 minutes, 200 ml of 80% ethanol aqueous solution was added to the mixture and well stirred. The antioxidant was then extracted. The extract was centrifuged (2,500 rpm, 10 minutes) and the supernatant was collected. After 200 ml of 80% ethanol aqueous solution was added to the cell debris, the mixture was extracted. The extracts obtained by extraction with ethanol aqueous solution 3 times were collected and evaporated at 40° C. to dryness with a rotary evaporator to give 4.8 g of the yellowish brown extract.

EXAMPLE 2

After 3 liters of medium having the composition shown in Table 1 was charged in a plant cell culture tank of 5 liter volume equipped with an aerial stirrer, the medium was sterilized at 120° C. for 20 minutes in an autoclave under pressure. Separately, 60 ml of medium having the composition shown in Table 1 was charged in an Erlenmeyer's flask of 300 ml and sterilized in a similar manner. Seeds of sesame culture cells were added to the medium and shake-cultured at 35° C. under a fluorescent light under the shake number of 60 rpm. The culture cells corresponding to 5 flasks cultured for 7 days were recovered by aseptic operation and inoculated in the plant cell culture tank. Culture conditions of the plant cell culture tank were: stirring number of 30 rpm, pH of $5.7 \pm 0.1$, aerial amount of 1.5 liter/min, light exposure of 8,000 lux, and temperature of 35° C. for 10 days. After completion of the culture, the culture broth was centrifuged to recover the cells. On a dry weight basis, 43 g of the cells were obtained.

Using 500 g of the sesame cells obtained by culture, the antioxidant was extracted and purified. That is, 1.9 liter of ethanol was added to the sesame cells. While stirring with a homogenizer, extraction was performed for 20 minutes. Then, the cells and the extract were separated from each other through a filter. After 2 liters of 80% ethanol water was added to the cell debris, extraction was performed for 20 minutes in a similar manner. The cell debris was then isolated through a filter and further extracted with 2 liters of 80% ethanol.

The extracts were combined and concentrated at 40° C. under reduced pressure to give 11.4 g of brown crude extract.

Amberlite XAD-II used for adsorption chromatography was packed in a glass-made column having a diameter of 5 cm and a length of 30 cm. Water was passed through the column to equilibrate. To the column was overlaid 5 g of the extract in such a state that the resin was adsorbed on the upper part of the column. By stepwise elution with water and with methanol while sequentially increasing its concentration, the desired substance was eluted. The fraction eluted with 60% methanol was collected and concentrated at 40° C. under reduced pressure to give 210 mg of the yellowish brown intermediary product. High performance liquid chromatography of this product was repeated until single peak was obtained. As the result, there were obtained, as the purified substances, 6 mg of Substance 1, 13 mg of Substance 2 and 18 mg of Substance 3.

The antioxidative activity of the three Substances was determined by the rabbit erythrocyte membrane ghost method. The respective antioxidative activities were as potent as butylhydroxyanisole (BHA).

TEST EXAMPLE

Excellent antioxidative activity of the antioxidant prepared by the present invention was confirmed as follows.

The extract, 100 mg, obtained in EXAMPLE 1 was dissolved in 100 ml of 80% ethanol aqueous solution (in a concentration of 1 mg/ml) to make an analytical sample of the antioxidative activity. Using 1 ml of the above solution as a sample, the degree of prevention of linoleic acid from autoxidation was determined by the rhodan iron method. As the result, it was confirmed that the antioxidant having a high activity equivalent to that of $\alpha$-tocopherol (0.2 mg) or butylhydoxyanisole (BHA, 0.2 mg) was contained in the sample (1 mg). extracted from the sesame culture cells, as is also clear from FIG. 19.

INDUSTRIAL APPLICABILITY

The glycoside of the present invention having the antioxidative activity exhibits an excellent antioxidative property and is extracted from the medium obtained by culturing sesame cells grown at a high temperature. Therefore, according to the present invention, antioxidative glycosides derived from natural matters can be supplied systematically in large quantities. Thus, the present invention may be utilized as foods, drugs and cosmetics.

What is claimed is:

1. A glycoside represented by the following structural formula (A):

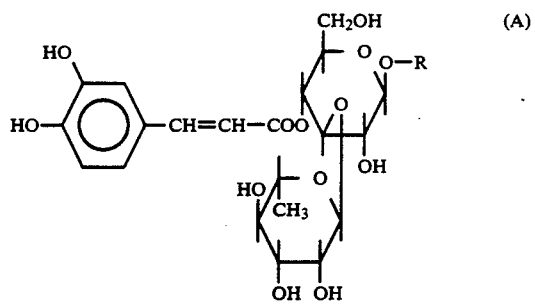

wherein R is

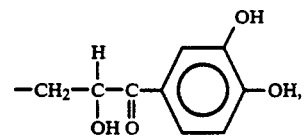

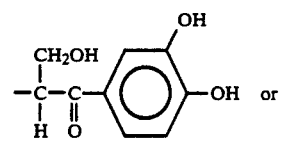

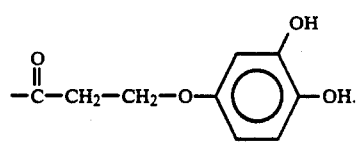

2. An antioxidative composition comprising, as an effective ingredient, at least one of the three substances of the glycoside represented by structural formula (A) as set forth in claim 1 in an effective amount and an edible or pharmaceutically acceptable carrier or diluent.

* * * * *